United States Patent
Zou et al.

(10) Patent No.: US 12,161,685 B2
(45) Date of Patent: Dec. 10, 2024

(54) MULTI-EFFICACY TRADITIONAL CHINESE MEDICINE COMPOUND COMPOSITION AND APPLICATION THEREOF IN PHARMACEUTICAL PREPARATIONS

(71) Applicants: Chenland Nutritionals Inc.; Qingdao Chenland Pharmaceutical Technology Development Co., Ltd., Qingdao (CN)

(72) Inventors: Shengcan Zou, Qingdao (CN); Zengliang Zhang, Qingdao (CN); Min Wang, Qingdao (CN); Zhuqing Liu, Qingdao (CN); Sai Lu, Qingdao (CN); Li Li, Qingdao (CN); Shanglong Wang, Qingdao (CN)

( * ) Notice: Subject to any disclaimer, the term of this patent is extended or adjusted under 35 U.S.C. 154(b) by 588 days.

(21) Appl. No.: 17/213,340

(22) Filed: Mar. 26, 2021

(65) Prior Publication Data

US 2022/0241362 A1    Aug. 4, 2022

Related U.S. Application Data

(63) Continuation of application No. PCT/CN2020/122398, filed on Oct. 21, 2020.

(30) Foreign Application Priority Data

Oct. 19, 2020 (CN) .......................... 202011118549.2

(51) Int. Cl.
    *A61K 36/296* (2006.01)
    *A61K 31/7008* (2006.01)
    *A61K 31/737* (2006.01)
    *A61K 36/537* (2006.01)
    *A61K 36/8945* (2006.01)
    *A61K 38/01* (2006.01)

(52) U.S. Cl.
    CPC ........ *A61K 36/296* (2013.01); *A61K 31/7008* (2013.01); *A61K 31/737* (2013.01); *A61K 36/537* (2013.01); *A61K 36/8945* (2013.01); *A61K 38/014* (2013.01)

(58) Field of Classification Search
    None
    See application file for complete search history.

(56) References Cited

U.S. PATENT DOCUMENTS

| 11,331,339 | B2 * | 5/2022 | Zou ......................... A61K 47/42 |
| 2017/0095539 | A1 * | 4/2017 | Tan ........................ A61K 36/185 |
| 2020/0237805 | A1 * | 7/2020 | Zou ..................... A61K 31/7008 |

FOREIGN PATENT DOCUMENTS

CN    110558561 A    * 12/2019    .......... A23L 33/105

* cited by examiner

*Primary Examiner* — Dominic Lazaro

(57) ABSTRACT

A multi-efficacy traditional Chinese medicine compound composition and application thereof in pharmaceutical preparations are disclosed. The traditional Chinese medicine extracts are combined with the glucosamine, the collagen and the chondroitin sulfate, so that the multi-efficacy traditional Chinese medicine compound composition is prepared. The traditional Chinese medicine compound composition starts from improving the health of bone and joint and accompanying cardiovascular disease, selects the medicinal materials, and optimizes the extraction process of the traditional Chinese medicine for the diseases dominated by degenerative osteoarthritis. The disclosure has the efficacious of improving the symptoms of degenerative osteoarthritis, reducing blood pressure, improving the symptoms with osteoporosis, improving the symptoms with cardiovascular disease, improving the symptoms with urinary system disease, etc. It also has the characteristics of less dosage, significant curative effect and various functions, which is suitable for market promotion and application.

6 Claims, No Drawings

MULTI-EFFICACY TRADITIONAL CHINESE MEDICINE COMPOUND COMPOSITION AND APPLICATION THEREOF IN PHARMACEUTICAL PREPARATIONS

CROSS-REFERENCE TO RELATED APPLICATIONS

This application is a continuation of International Patent Application No. PCT/CN2020/122398 with a filing date of Oct. 21, 2020, designating the United States, and further claims priority to Chinese Patent Application No. 202011118549.2 with a filing date of Oct. 19, 2020. The content of the aforementioned applications, including any intervening amendments thereto, are incorporated herein by reference.

TECHNICAL FIELD

The present disclosure relates to the technical field of natural medicines, in particular to a formula of a compound composition and application thereof, and more specifically, to a multi-efficacy traditional Chinese medicine compound composition and application thereof in pharmaceutical preparations.

BACKGROUND

Osteoarthritis is a common degenerative disease, its occurrence is related to articular cartilage damage, mainly characterized by articular cartilage degeneration, destruction and bone hyperplasia. China has gradually entered an aging society. The impact of osteoarthritis on human health and the medical costs are increasing year by year at an alarming rate. Some data show that osteoarthritis has become the second major disease after heart disease, which makes the patients lose the ability to work. It brings heavy economic burden to the family and society, which has aroused widespread concern of professionals at home and abroad. In clinic, many patients with knee osteoarthritis mainly have cold pain and tenderness of knee joint, limited joint activity, joint swelling or deformity, joint weakness, bone friction and other symptoms, accompanied by numbness, pain and limb weakness and other symptoms.

Osteoporosis is a common disease, which is characterized by bone loss, destruction of bone microstructure and increase of bone fragility, resulting in an increased risk of fracture, especially in the spine, hip, wrist, proximal humerus and pelvis. Osteoporosis has a high incidence rate in the middle and old aged population. At present, there are about 90 million osteoporosis patients in China. Among them, the elderly people over 60 years old account for 56%, and all of the 60%~70% patients are postmenopausal women. When osteoporosis develops to a serious stage, brittle fracture will occur, which will bring heavy burden to the family and society. Once complicated with cardiovascular and cerebrovascular diseases, it will pose a great threat to the life and health of the elderly. China is a country with a large population. With the acceleration of population aging, the problem of osteoporotic fracture has become the top priority.

Cardiovascular and cerebrovascular disease is the general name of cardiovascular diseases and cerebrovascular diseases, which generally refers to the ischemic or hemorrhagic diseases of the heart, brain and systemic tissues caused by hyperlipidemia, blood viscosity, atherosclerosis, hypertension and so on. With the continuous development and progress of society, the development of cardiovascular disease is on the rise. It has overtaken cancer and become the main cause of death and disability all over the world. Although the treatment level of cardiovascular disease is constantly improving, and the treatment methods such as drugs, interventions and surgery are developing rapidly, the prevalence and mortality of cardiovascular disease in China are still rising, and the mortality is still in the first place. The common symptoms of cardiovascular disease include palpitation, shortness of breath, orthopnea, paroxysmal dyspnea at night, compression or constriction pain behind sternum, chest tightness, edema, cyanosis, syncope, cough, hemoptysis, weakness, belching, epigastric pain, nausea, vomiting; left back pain, left arm pain, etc.

Hypertension can aggravate the heart load and lead to left ventricular hypertrophy, which further leads to hypertensive heart disease and heart failure. Long term hypertension can thicken or harden the wall of arteries and narrow the lumen, thus affecting the blood supply to the heart and brain. When the blood pressure rises suddenly, the cerebral blood vessels are easy to rupture and produce cerebral hemorrhage; or the hardened cerebral arterioles form a kind of chestnut sized micro aneurysm, and when the blood fluctuates, the micro artery flow breaks and causes cerebral hemorrhage; or hypertension accelerates the process of arteriosclerosis, and the arterial endothelial cells are damaged, and the platelets are easy to gather in the injured area, and it is easy to form thrombosis, leading to myocardial infarction or cerebral infarction.

The diseases of urinary system can be caused by the diseases of other systems of the body, and can also affect other systems and even the whole body. It is mainly manifested in the urinary system itself, such as changes in micturition, changes in urine, lumps, pain, etc., but also in other aspects, such as hypertension, edema, anemia, etc. Because of the great harm of urinary tract infection, people generally have some panic psychology. Some people think too much about privacy protection, which leads to various cognitive and behavioral deviations in the treatment. The traditional concept makes trouble, and the lack of regular hospital treatment increases the difficulty of treatment.

In the existing technology, western medicine and surgery are the main treatment methods for the above diseases, and some Chinese patent medicines have become conventional drugs for the treatment of these diseases. But these methods often have big side effects and high risks. And most of the existing drugs have single efficacy, patients need to take more than two or three kinds of drugs at the same time, which is high cost and inconvenient.

To sum up, it is an urgent problem for those skilled in the art to develop a multi-efficacy traditional Chinese medicine compound composition to comprehensively treat the above diseases.

SUMMARY OF THE INVENTION

In view of this, the object of the invention is to provide a multi-efficacy Chinese medicine compound composition aiming at the problems existing in the prior art.

Technical solutions of the present invention are specifically described as follows. In the first aspect, the invention provides a multi-efficacy traditional Chinese medicine compound composition, composed of the following raw materials in parts by weight:

0.5~2.0 parts of glucosamine;
0.5~1.5 parts of collagen;
0.1~1.0 parts of chondroitin sulfate; and 0.3~1.5 parts of traditional Chinese medicine extracts.

Preferably, the traditional Chinese medicine compound composition is composed of the following raw materials in parts by weight:
0.7~1.0 parts of glucosamine;
0.5~0.8 parts of collagen;
0.2~0.5 parts of chondroitin sulfate; and
0.5~0.7 parts of traditional Chinese medicine extracts.

Preferably, the traditional Chinese medicine compound composition is composed of the following raw materials in parts by weight:
0.8 parts of glucosamine;
0.6 parts of collagen;
0.3 parts of chondroitin sulfate; and
0.55 parts of traditional Chinese medicine extracts.

According to the theory of modern medicine and traditional Chinese medicine, the multi-efficacy traditional Chinese medicine compound composition is selected from the aspects of improving the health of bone and joint and accompanying cardiovascular disease, and the traditional Chinese medicine is optimized for the disease dominated by degenerative osteoarthritis, so as to further increase the curative effect. The invention not only has the functions of improving the symptoms of degenerative osteoarthritis, reducing blood pressure, improving the symptoms with osteoporosis, improving the symptoms with cardiovascular disease, improving the symptoms with urinary system disease and so on, but also has the characteristics of small dosage, remarkable curative effect, various functions and so on.

Specifically, the mechanism of the traditional Chinese medicine compound composition in improving the symptoms of degenerative osteoarthritis, reducing blood pressure, improving the symptoms with osteoporosis, improving cardiovascular and cerebrovascular diseases and/or improving urinary system diseases, and the correlation between various diseases are as follows:

Osteoarthritis is also known as degenerative osteoarthritis. On the one hand, it is mainly due to the age-related degenerative changes of articular cartilage, resulting in joint pain, limited activity or joint deformity, walking difficulties and other symptoms. On the other hand, it is also due to the age-related bone loss in the elderly, which makes the elderly prone to osteoporosis. Osteoporosis is the pathological basis of other joint diseases in the elderly, which can lead to other bone diseases to a certain extent. In addition, related studies have shown that patients with osteoarthritis are prone to complicated with cardiovascular and cerebrovascular diseases, diabetes, lung disease and other diseases.

Cardiovascular and cerebrovascular diseases are common diseases in the health of the middle-aged and elderly people over 50 years old. Common coronary heart disease, cerebral thrombosis, angina pectoris, atherosclerosis, hypertension and hyperlipidemia are cardiovascular and cerebrovascular diseases, which can cause chest tightness, palpitation, palpitation, shortness of breath, stroke, limb weakness, language disorder, unstable standing, chest pain, chest tingling and other symptoms. Among them, hypertension is a common disease in elderly cardiovascular and cerebrovascular diseases. Rising blood pressure can lead to cerebral hemorrhage, accelerated arteriosclerosis, cerebral infarction and other serious problems. At the same time, the studies found that many patients with hypertension are accompanied by urinary system diseases, which may be caused by hypertension, hyperlipidemia and other factors.

With the gradual improvement of people's living standards, the acceleration of population aging and the change of lifestyle, the health problems of the elderly are often accompanied by the complications of a variety of diseases. Various diseases interact with each other, usually not a single symptom. The traditional Chinese medicine selected in the invention has the traditional effects of promoting blood circulation to relieve pain, expelling wind and removing dampness, relaxing channels and collaterals, tonifying kidney yang, etc., and is supplemented with modern scientific ingredients such as glucosamine, chondroitin sulfate and collagen, so as to supplement the ingredients easily missing or lost by the elderly from the perspective of modern medicine. Starting from multiple angles at the same time, it has an overall treatment and improvement effect on the elderly's syndrome.

Preferably, the traditional Chinese medicine extracts are prepared by extracting the traditional Chinese medicine materials, and the traditional Chinese medicine extracts are composed of following extracts according to the mass percentage:
25~40% of *Epimedii Folium* extract;
3~7% of *Salvia Miltiorrhizae* extract; and
55~75% of *Dioscoreae Nipponicae Rhizoma* extract.

Preferably, the traditional Chinese medicine extracts are composed of following extracts according to the mass percentage:
25~34% of *Epimedii Folium* extract;
4~4.8% of *Salvia Miltiorrhizae* extract; and
50-70% of *Dioscoreae Nipponicae Rhizoma* extract.

It should be noted that, the raw materials of the extracts used herein are scientifically selected and combined organically according to the compatibility of traditional Chinese medicines rather than simple superimposing of the effect of each Chinese medicine. Effects of the abovementioned traditional Chinese medicine materials are listed as follows.

*Dioscoreae Nipponicae Rhizoma*

Functions: dispelling wind and dampness, relieving muscles and collaterals, promoting blood circulation and relieving pain, relieving cough and relieving asthma;

Indications: rheumatic arthralgia, joint swelling, pain and numbness, fall and flutter injury, flashing waist and qi, cough and wheezing.

*Epimedii Folium*

Functions: nourishing kidney yang, strengthening muscles and bones, dispelling rheumatism.

Indications: deficiency of kidney Yang, impotence and nocturnal emission, soft muscles and bones, rheumatic arthralgia, numbness and contracture.

*Salvia Miltiorrhizae*

Functions: invigorating blood circulation and removing blood stasis, relieving menstruation and relieving pain, clearing heart and relieving irritation, cooling blood and eliminating carbuncle Indications: chest pain, abdominal pain, abdominal pain, gallbladder accumulation, heat pain, upset and insomnia, irregular menstruation, dysmenorrhea, amenorrhea, sore swelling and pain.

Through the efficacy analysis of the above plant medicinal materials, the Chinese medicinal materials selected in the invention are the classic prescriptions extracted from Chinese Pharmacopoeia and traditional Chinese medicine classic prescriptions, and on the basis of the prescriptions, the optimization is carried out in combination with scientific research and the extraction of the effective components.

Among them, *Dioscoreae Nipponicae Rhizoma* is used to dispel rheumatism, promotes blood circulation and clears the collaterals as monarch medicine; *Epimedii Folium* is used to enter the liver and kidney meridians, nourishes the kidney and strengthens Yang, dispels wind and dampness, treats impotence of kidney deficiency, weakness of waist and knees, wind-cold dampness, spleen, muscles and bones pain, etc. as minister medicine; *Salvia Miltiorrhizae* is used to activate blood circulation, and reduce dryness of *Epimedii Folium* as adjuvant medicine.

In addition, though the common dosage of each traditional Chinese medicine is known in the prior art, the prescription of the disclosure is made for the target disease by organically combining the above medicines, and its medicinal effect is not equivalent to the simple superposition of the effects of these medicines at a commonly-used amount. Actually, it cannot determine the amount of each medicine in the prescription according to their individual commonly-used amount, and the compounding ratio depends on many factors such as the characteristics of the medicinal materials and the compatibility of monarch drugs, ministerial drugs, adjuvant drugs and envoy drugs, and cannot be determined by experimental means such as comparison method and orthogonal test.

According to the requirements of Pharmacopoeia, the invention carries out content determination and fingerprint of effective components (dioscin, protodioscin or total saponin, icariin or diglycoside, tanshinone IIA, cryptotanshinone or salvianolic acid B) in various traditional Chinese medicine extracts, and scientifically controls the content of effective components in various traditional Chinese medicine extracts, so as to ultimately improve the efficacy.

Preferably, an extraction process of the *Dioscoreae Nipponicae Rhizoma* extract comprises the following steps:

1) subjecting *Dioscoreae Nipponicae Rhizoma* material to extraction with a 50-70% ethanol solution in a volume ratio of 1:7~15, heating reflux 2~3 times for 1~2 h each time and filtration to obtain filtrates;

2) combining the filtrates, purifying, concentrating, and adding with 10% β-cyclodextrintoto; continuously subjecting the combined filtrate to spray drying at 200° C.; and sieving the dried product with a sieve of 80 mesh to produce the *Dioscoreae Nipponicae Rhizoma* extract.

Preferably, an extraction process of the *Dioscoreae Nipponicae Rhizoma* extract comprises the following steps:

1) subjecting *Dioscoreae Nipponicae Rhizoma* material to extraction with a 70% ethanol solution in a volume ratio of 1:15, heating reflux twice for 2 h each time and filtration to obtain filtrates;

2) combining the filtrates, purifying, concentrating, and adding with 10% β-cyclodextrintoto; continuously subjecting the combined filtrate to spray drying at 200° C.; and sieving the dried product with a sieve of 80 mesh to produce the *Dioscoreae Nipponicae Rhizoma* extract.

In a second aspect, the invention provides an application of the multi-efficacy traditional Chinese medicine compound composition in pharmaceutical preparations.

The pharmaceutical preparations are prepared by mixing the traditional Chinese medicine compound composition and auxiliary materials according to a mass ratio of 100:(0.2~2).

Further, the application in pharmaceutical preparations includes improving the symptoms of degenerative osteoarthritis, reducing blood pressure, improving the symptoms with osteoporosis, improving cardiovascular and cerebrovascular diseases and/or improving diseases with urinary system.

Specifically, after 90 days of trial administration of the traditional Chinese medicine compound composition disclosed by the disclosure, the effective rate of improving the symptoms of knee joint disease was 89.80%; the effective rate of left knee extension and flexion was 59.49%; the effective rate of right knee extension and flexion was 65.82%; the effective rate of improving osteoporosis related pain was 74.19%; the effective rate of improving cardiovascular and cerebrovascular diseases related problems is 68.97%; the effective rate of reducing diastolic blood pressure was 73.75%, and the effective rate of reducing systolic blood pressure was 76.24%; and the effective rate of improving symptoms related to urinary system diseases was 76.54%.

Compared to the prior art, the invention has the following beneficial effects:

In the invention, the traditional Chinese medicine extracts are combined with the glucosamine, the collagen and the chondroitin sulfate, that is, the traditional Chinese medicine is combined with the modern components, so that the multi-efficacy traditional Chinese medicine compound composition is prepared.

The traditional Chinese medicine used in the traditional Chinese medicine extracts disclosed by the disclosure is referred to Chinese Pharmacopoeia, traditional Chinese medicine classical prescriptions and network pharmacology, and is selected according to scientific research, and the traditional Chinese medicine is complementary and coordinated. And from the aspects of improving bone and joint health and cardiovascular disease, through the control of raw materials and effective components of the extracts, the effectiveness of the prescription can be scientifically guaranteed.

By optimizing and improving the extraction process of *Dioscoreae Nipponicae Rhizoma*, the disclosure not only improves the content of diosgenin, protodiosgenin and total saponin in *Dioscoreae Nipponicae Rhizoma* extract, but also effectively ensures the stability of extraction process and extraction quality.

The traditional Chinese medicine compound composition protected by the invention firstly starts from improving the health of bone and joint and accompanying cardiovascular disease, selects the medicinal materials, and optimizes the extraction process of the traditional Chinese medicine for the diseases dominated by degenerative osteoarthritis. The pharmaceutical preparations of the invention have the efficacious of improving the symptoms of degenerative osteoarthritis, reducing blood pressure, improving the symptoms with osteoporosis, improving the symptoms with cardiovascular disease, improving the symptoms with urinary system disease, etc. It also has the characteristics of less dosage, significant curative effect and various functions, which is suitable for market promotion and application.

DETAILED DESCRIPTION OF EMBODIMENTS

Technical solutions of the present disclosure will be clearly and completely described below with reference to the embodiments. Obviously, described below are merely some embodiments of the disclosure, rather than all the embodiments. Other embodiments made by those skilled in the art without sparing any creative effort should fall within the scope of the disclosure.

The disclosure provides a multi-efficacy traditional Chinese medicine compound composition and application thereof in pharmaceutical preparations. The compound composition not only has the effect of promoting bone and joint health, but also has the excellent effect of improving osteoporosis related pain, improving cardiovascular disease related symptoms, reducing blood pressure and improving urinary system diseases.

The disclosure will be further described below with reference to the embodiments. It should be understood that these embodiments are merely illustrative of the disclosure, and are not intended to limit the disclosure. Any non-essential improvement and modification made by those skilled in the art without departing from the content of the disclosure should still fall within the scope of the disclosure.

The technical scheme disclosed by the disclosure will be further described in combination with specific embodiments.

Embodiment 1

Provided herein was a multi-efficacy traditional Chinese medicine compound composition, composed of the following raw materials in parts by weight:
  1.2 parts of glucosamine;
  0.8 parts of collagen;
  0.5 parts of chondroitin sulfate; and
  0.35 parts of traditional Chinese medicine extracts.

The compound composition was added with 0.5% magnesium stearate, evenly mixed according to the weight ratio, and put into the capsules to obtain the capsule preparation of the traditional Chinese medicine compound composition.

Embodiment 2

Provided herein was a multi-efficacy traditional Chinese medicine compound composition, composed of the following raw materials in parts by weight:
  1.0 parts of glucosamine;
  0.5 parts of collagen;
  0.4 parts of chondroitin sulfate; and
  0.5 parts of traditional Chinese medicine extracts.

The compound composition was added with 0.5% magnesium stearate, evenly mixed according to the weight ratio, and put into the capsules to obtain the capsule preparation of the traditional Chinese medicine compound composition.

Embodiment 3

Provided herein was a multi-efficacy traditional Chinese medicine compound composition, composed of the following raw materials in parts by weight:
  0.6 parts of glucosamine;
  0.5 parts of collagen;
  0.35 parts of chondroitin sulfate; and
  0.6 parts of traditional Chinese medicine extracts.

The compound composition was added with 0.5% magnesium stearate, evenly mixed according to the weight ratio, and put into the capsules to obtain the capsule preparation of the traditional Chinese medicine compound composition.

Embodiment 4

Provided herein was a multi-efficacy traditional Chinese medicine compound composition, composed of the following raw materials in parts by weight:
  0.8 parts of glucosamine;
  0.6 parts of collagen;
  0.3 parts of chondroitin sulfate; and
  0.55 parts of traditional Chinese medicine extracts.

The compound composition was added with 0.5% magnesium stearate, evenly mixed according to the weight ratio, and put into the capsules to obtain the capsule preparation of the traditional Chinese medicine compound composition.

Embodiment 5

The composition of the traditional Chinese medicine extracts in any one of the multi-efficacy traditional Chinese medicine compound composition disclosed in the above embodiments 1 to 4 was as follows, by weight parts:
  38.4% of *Epimedii Folium* extract, 5.8% of *Salvia Miltiorrhizae* extract; and 55.8% of *Dioscoreae Nipponicae Rhizoma* extract.

The preparation method of the traditional Chinese medicine extracts was as follows:
  each material was extracted by alcohol extraction process, purified and concentrated by macroporous resin, and dried by spraying with 10% β-cyclodextrinto.

Embodiment 6

The composition of the traditional Chinese medicine extracts in any one of the multi-efficacy traditional Chinese medicine compound composition disclosed in the above embodiments 1 to 4 was as follows, by weight parts:
  36.5% of *Epimedii Folium* extract, 4.8% of *Salvia Miltiorrhizae* extract; and 58.7% of *Dioscoreae Nipponicae Rhizoma* extract.

The preparation method of the traditional Chinese medicine extracts was as follows:
  each material was extracted by alcohol extraction process, purified and concentrated by macroporous resin, and dried by spraying with 10%β-cyclodextrinto.

Embodiment 7

The composition of the traditional Chinese medicine extracts in any one of the multi-efficacy traditional Chinese medicine compound composition disclosed in the above embodiments 1 to 4 was as follows, by weight parts:
  28.08% of *Epimedii Folium* extract, 4.3% of *Salvia Miltiorrhizae* extract; and 67.62% of *Dioscoreae Nipponicae Rhizoma* extract.

The preparation method of the traditional Chinese medicine extracts was as follows:
  each material was extracted by alcohol extraction process, purified and concentrated by macroporous resin, and dried by spraying with 10%β-cyclodextrinto.

Embodiment 8

The composition of the traditional Chinese medicine extracts in any one of the multi-efficacy traditional Chinese medicine compound compositions disclosed in the above embodiments 1 to 4 was as follows, by weight parts:
  36.5% of *Epimedii Folium* extract, 4.8% of *Salvia Miltiorrhizae* extract; and 58.7% of *Dioscoreae Nipponicae Rhizoma* extract.

The preparation method of the traditional Chinese medicine extracts was as follows:
  (1) *Epimedii Folium* material was subjected to extraction with a 70% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Epimedii Folium* extract;
  (2) *Salvia Miltiorrhizae* material was subjected to extraction with a 80% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Salvia Miltiorrhizae* extract;
(3) *Dioscoreae Nipponicae Rhizoma* material was subjected to extraction with a 70% ethanol solution in a volume ratio of 1:8, heating reflux three times for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Dioscoreae Nipponicae Rhizoma* extract;
(4) The prepared traditional Chinese medicine extracts were mixed and evenly mixed according to the ratio of 0.55 parts of the traditional Chinese medicine extracts, 0.8 parts of glucosamine, 0.6 parts of collagen and 0.3 parts of chondroitin sulfate to obtain a compound composition with 100 times daily prescription dose.

The compound composition was added with 0.5% magnesium stearate, evenly mixed according to the weight ratio, and put into the capsules to obtain the capsule preparation of the traditional Chinese medicine compound composition.

Embodiment 9

The composition of the traditional Chinese medicine extracts in the multi-efficacy traditional Chinese medicine compound composition disclosed in the above embodiment 1 was as follows, by weight parts:

36.5% of *Epimedii Folium* extract, 4.8% of *Salvia Miltiorrhizae* extract; and 58.7% of *Dioscoreae Nipponicae Rhizoma* extract.

The preparation method of the traditional Chinese medicine extracts was as follows:
(1) *Epimedii Folium* material was subjected to extraction with a 70% ethanol solution in a volume ratio of 1:10, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Epimedii Folium* extract;
(2) *Salvia Miltiorrhizae* material was subjected to extraction with a 70% ethanol solution in a volume ratio of 1:12, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Salvia Miltiorrhizae* extract;
(3) *Dioscoreae Nipponicae Rhizoma* material was subjected to extraction with a 70% ethanol solution in a volume ratio of 1:15, heating reflux twice for 2 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Dioscoreae Nipponicae Rhizoma* extract;
(4) The prepared traditional Chinese medicine extracts were mixed and evenly mixed according to the ratio of 0.55 parts of the traditional Chinese medicine extracts, 0.8 parts of glucosamine, 0.6 parts of collagen and 0.3 parts of chondroitin sulfate to obtain a compound composition with 100 times daily prescription dose.

The compound composition was added with 0.5% magnesium stearate, evenly mixed according to the weight ratio, and put into the capsules to obtain the capsule preparation of the traditional Chinese medicine compound composition.

Embodiment 10

The composition of the traditional Chinese medicine extracts in the multi-efficacy traditional Chinese medicine compound composition disclosed in the above embodiment 1 was as follows, by weight parts:

28.08% of *Epimedii Folium* extract, 4.3% of *Salvia Miltiorrhizae* extract; and 67.67% of *Dioscoreae Nipponicae Rhizoma* extract.

The preparation method of the traditional Chinese medicine extracts was as follows:
(1) *Epimedii Folium* material was subjected to extraction with a 70% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Epimedii Folium* extract;
(2) *Salvia Miltiorrhizae* material was subjected to extraction with a 80% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Salvia Miltiorrhizae* extract;
(3) *Dioscoreae Nipponicae Rhizoma* material was subjected to extraction with a 70% ethanol solution in a volume ratio of 1:15, heating reflux twice for 2 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Dioscoreae Nipponicae Rhizoma* extract;
(4) The prepared traditional Chinese medicine extracts were mixed and evenly mixed according to the ratio of 0.55 parts of the traditional Chinese medicine extracts, 0.8 parts of glucosamine, 0.6 parts of collagen and 0.3 parts of chondroitin sulfate to obtain a compound composition with 100 times daily prescription dose.

The compound composition was added with 1.5% magnesium stearate, evenly mixed according to the weight ratio, and put into the capsules to obtain the capsule preparation of the traditional Chinese medicine compound composition.

The content of the disclosure is not limited to the contents of the above-mentioned embodiments, and the combination of one or several embodiments can also realize the purpose of the disclosure.

Comparative Embodiment 1

Compared with embodiment 9, the composition of the traditional Chinese medicine extracts in the traditional Chinese medicine compound composition was as follows, by weight parts:

28.08% of *Epimedii Folium* extract, 4.3% of *Salvia Miltiorrhizae* extract; and 67.67% of *Dioscoreae Nipponicae Rhizoma* extract.

The preparation method of the traditional Chinese medicine extracts was as follows:
(1) *Epimedii Folium* material was subjected to extraction with a 70% ethanol solution in a volume ratio of 1:8, heating refluxg twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Epimedii Folium* extract;

(2) *Salvia Miltiorrhizae* material was subjected to extraction with a 80% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Salvia Miltiorrhizae* extract;

(3) *Dioscoreae Nipponicae Rhizoma* material was subjected to extraction with a 70% ethanol solution in a volume ratio of 1:8, heating refluxg three times for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Dioscoreae Nipponicae Rhizoma* extract.

The prepared traditional Chinese medicine extracts were mixed and evenly mixed according to the ratio of 0.55 parts of the traditional Chinese medicine extracts, 0.8 parts of glucosamine, 0.6 parts of collagen and 0.3 parts of chondroitin sulfate to obtain a compound composition with 100 times daily prescription dose.

The compound composition was added with 0.5% magnesium stearate, evenly mixed according to the weight ratio, and put into the capsules to obtain the capsule preparation of the traditional Chinese medicine compound composition.

Comparative Embodiment 2

Compared with embodiment 9, the composition of the traditional Chinese medicine extracts in the traditional Chinese medicine compound composition was as follows, by weight parts:

36.5% of *Epimedii Folium* extract, 4.8% of *Salvia Miltiorrhizae* extract; and 58.7% of *Dioscoreae Nipponicae Rhizoma* extract.

The preparation method of the traditional Chinese medicine extracts was as follows:

(1) *Epimedii Folium* material was subjected to extraction with a 70% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Epimedii Folium* extract;

(2) *Salvia Miltiorrhizae* material was subjected to extraction with a 80% ethanol solution in a volume ratio of 1:8, heating reflux twice for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Salvia Miltiorrhizae* extract;

(3) *Dioscoreae Nipponicae Rhizoma* material was subjected to extraction with a 70% ethanol solution in a volume ratio of 1:15, heating reflux three times for 1.5 h each time and filtration to obtain filtrates; the filtrates were combined, purified, concentrated, added with 10% β-cyclodextrintoto and subjected to pray drying at 200° C.; and the dried product was sieved with a sieve of 80 mesh to produce the *Dioscoreae Nipponicae Rhizoma* extract.

The prepared traditional Chinese medicine extracts were mixed and evenly mixed according to the ratio of 0.55 parts of the traditional Chinese medicine extracts, 0.8 parts of glucosamine, 0.6 parts of collagen and 0.3 parts of chondroitin sulfate to obtain a compound composition with 100 times daily prescription dose.

The compound composition was added with 0.5% magnesium stearate, evenly mixed according to the weight ratio, and put into the capsules to obtain the capsule preparation of the traditional Chinese medicine compound composition.

In order to verify the excellent effect of the traditional Chinese medicine compound composition disclosed and protected by the disclosure, embodiments 1 to 4 and comparative embodiments 1 and 2 of the traditional Chinese medicine compound composition were tested. The test method and results are as follows:

1. Effect of Improving Osteoarthritis (1) Basic Information

The products provided in embodiments 1 to 4 and comparative embodiments 1 and 2 were taken as test samples. In this study, 196 people who have been diagnosed with knee arthritis but no other joint pain caused by bone spur were selected as experience personnel. The experience personnel should avoid using prescription drugs, OTC, supplements and food/beverage during the use of this product, and should stop using it for more than 2 weeks (14 days) before the start of the experience. The experience personnel agreed to go to the designated hospital for three times (on day 0, day 30 and day 90 respectively) for physical examination of blood, blood pressure, electrocardiogram, urine, knee extension and flexion measurement and other related items, and truthfully provided all the reports.

(2) Diagnostic Criteria

1) Safety observation: 12 items of blood routine, 8 items of urine routine, 7 items of liver function, 2 items of renal function, ECG;

2) Efficacy indicators: MRI, blood pressure, knee flexion and extension, vascular regulatory factors, hormone levels;

3) 11 symptoms of knee joint disease: pain when walking on flat ground, pain when standing, pain when going up and down stairs, pain when resting, pain when standing from the seat, bone friction and frications in daily activities, stiffness of joints in the morning, stiffness of joints after sitting or lying down in the daytime, swelling of knee joints, free flexion and extension of knee joints, auxiliary tools for standing and walking.

According to the degree of pain/stiffness/swelling/limitation, the symptoms were divided into grade I-IV, and the accumulate score were calculated. Grade I (0 point): asymptomatic; grade II (1 point): mild; grade III (2 points): moderate; grade IV (3 points): severe.

(3) Treatment Methods and Course of Treatment:

196 patients were randomly divided into group A and group B, with 98 patients in each group. Group A took the capsules of traditional Chinese medicine compound composition in embodiment 3, and group B took the capsules of traditional Chinese medicine compound composition in comparative embodiment 1, twice a day for each person, 2 capsules each time, with the dosage of 2.4 g/day for 90 consecutive days.

(4) Evaluation Criteria of Curative Effect

Nimodipine score method: (pre-experience score−post-experience score)/pre-experience score×100%

Effective: symptoms and signs improved; score reduced by more than 20%

Invalid: not reach the valid standard (5) Curative Effect a) Safety Observation

The results of white blood cells, red blood cells, hemoglobin and platelets showed no significant changes (P>0.05) before taking, 30 days and 90 days after taking; the results of heart rate showed no significant changes (P>0.05); chest X-ray, electrocardiogram, abdominal B-ultrasound and urine routine examination showed no significant abnormalities. The results are as follows:

TABLE 1

Results of blood routine examination before and after taking

| Project | 0 day | 30 days | P Value | 90 days | P Value |
|---|---|---|---|---|---|
| WBC count ($10^9$/L) | 5.87 ± 2.82 | 7.35 ± 3.46 | 0.4729 | 5.74 ± 2.76 | 0.9450 |
| Monocyte ratio (%) | 9.44 ± 0.97 | 8.43 ± 1.28 | 0.3176 | 8.45 ± 1.50 | 0.3769 |
| Monocyte count ($10^9$/L) | 0.66 ± 0.04 | 0.70 ± 0.20 | 0.7277 | 0.57 ± 0.10 | 0.2245 |
| Lymphocyte ratio (%) | 39.46 ± 12.53 | 38.82 ± 11.35 | 0.8701 | 36.85 ± 11.63 | 0.5086 |
| Neutrophil ratio (%) | 55.49 ± 14.99 | 55.54 ± 13.32 | 0.9933 | 57.01 ± 12.92 | 0.7693 |
| Neutrophil count ($10^9$/L) | 2.39 ± 1.87 | 2.68 ± 1.93 | 0.8123 | 2.56 ± 1.70 | 0.8834 |
| Red blood cell distribution width (%) | 11.15 ± 1.39 | 13.09 ± 1.25 | 0.1037 | 12.34 ± 11.67 | 0.1011 |
| Mean corpuscular volume (fl) | 90.36 ± 8.35 | 91.21 ± 8.56 | 0.8335 | 91.07 ± 7.98 | 0.8557 |
| Mean platelet volume (fl) | 9.76 ± 2.51 | 10.27 ± 1.56 | 0.6770 | 10.40 ± 11.39 | 0.5926 |
| Hematocrit (%) | 0.30 ± 0.07 | 0.31 ± 0.08 | 0.8535 | 0.28 ± 0.07 | 0.7225 |
| Mean hemoglobin (pg) | 31.37 ± 2.08 | 31.27 ± 2.33 | 0.9387 | 31.00 ± 2.37 | 0.7780 |
| Mean hemoglobin concentration (g/L) | 360.33 ± 1.70 | 345.00 ± 5.72 | 0.1220 | 338.33 ± 10.14 | 0.1390 |

TABLE 2

Examination of liver and kidney function and blood biochemical indexes

| Project | 0 day | 30 days | P Value | 90 days | P Value |
|---|---|---|---|---|---|
| x-protein (g/L) | 37.78 ± 1.24 | 38.78 ± 1.30 | 0.3713 | 39.55 ± 1.14 | 0.1176 |
| White ball ratio | 1.08 ± 0.08 | 1.38 ± 0.36 | 0.1395 | 1.17 ± 0.19 | 0.4205 |
| Triglyceride (mmol/L) | 2.44 ± 1.14 | 2.25 ± 0.95 | 0.4896 | 2.28 ± 0.94 | 0.5516 |
| High density lipoprotein (mmol/L) | 1.60 ± 0.50 | 1.60 ± 0.41 | 0.9865 | 1.47 ± 0.42 | 0.4923 |
| Low density lipoprotein (mmol/L) | 3.82 ± 0.79 | 3.63 ± 0.89 | 0.3120 | 3.40 ± 0.94 | 0.0363 |
| Total cholesterol (mmol/L) | 6.41 ± 0.94 | 6.14 ± 1.05 | 0.2399 | 5.80 ± 1.17 | 0.0151 |
| Fasting blood glucose (mmol/L) | 7.79 ± 1.66 | 7.33 ± 1.55 | 0.1857 | 7.40 ± 1.80 | 0.2912 |

TABLE 3

Analysis of heart rate before and after taking

| Project | Number | 0 day | 30 days | P Value | 90 days | P Value |
|---|---|---|---|---|---|---|
| Heart rate (BPM) | 55 | 70.37 ± 10.67 | 71.17 ± 11.82 | 0.6772 | 70.83 ± 11.15 | 0.8060 | b) Efficacy Evaluation

TABLE 4

Improving rate and effective rate of knee joint extension and flexion after taking

| Time | Project | Improving rate % | | Effective rate % (Effective number/total number) | |
|---|---|---|---|---|---|
| | | Comparative embodiment 1 | Embodiment 3 | comparative embodiment 1 | Embodiment 3 |
| 0 day | Left leg | / | / | / | / |
| | Right leg | / | / | / | / |
| 30 days | Left leg | 8.27% ± 10.21% | 11.17% ± 16.62% | 38.42% | 45.57% |
| | Right leg | 9.03% ± 11.27% | 11.96% ± 14.38% | 42.36% | 49.37% |

TABLE 4-continued

Improving rate and effective rate of knee joint extension and flexion after taking

| Time | Project | Improving rate % | | Effective rate % (Effective number/total number) | |
|---|---|---|---|---|---|
| | | Comparative embodiment 1 | Embodiment 3 | comparative embodiment 1 | Embodiment 3 |
| 90 days | Left leg | 11.24% ± 16.39% | 14.83% ± 27.18% | 47.88% | 59.49% |
| | Right leg | 13.57% ± 18.42% | 17.80% ± 27.78% | 56.74% | 65.82% |

TABLE 5

Changes of symptom accumulate score before and after taking

| Time | Comparative embodiment 1 | Embodiment 3 |
|---|---|---|
| 0 day | 15.31 ± 5.87 | 15.30 ± 6.08 |
| 30 days | 13.54 ± 6.03** | 11.81 ± 5.54** |
| 60 days | 11.87 ± 6.21**## | 9.39 ± 4.64**## |
| 90 days | 9.98 ± 5.24**## | 8.04 ± 4.68**##* |

Note:
compared with 0 day
*P < 0.05,
**P < 0.01; compared with 30 day
P < 0.05,
P < 0.01; compared with 60 day,
*P < 0.05.

TABLE 6

Overall efficacy evaluation

| | Comparative embodiment 1 | | | | Embodiment 3 | | | |
|---|---|---|---|---|---|---|---|---|
| Time/day | Number | Effective | invalid | Effective rate | Number | Effective | invalid | Effective rate |
| 7 | 98 | 23 | 75 | 23.46% | 98 | 31 | 67 | 30.63% |
| 14 | 98 | 35 | 63 | 35.71% | 98 | 52 | 46 | 53.06% |
| 21 | 98 | 44 | 54 | 44.90% | 98 | 63 | 35 | 64.29% |
| 30 | 98 | 49 | 49 | 50.89% | 98 | 71 | 27 | 72.45% |
| 45 | 98 | 60 | 38 | 61.22% | 98 | 81 | 17 | 82.65% |
| 60 | 98 | 70 | 28 | 71.43% | 98 | 84 | 14 | 85.71% |
| 90 | 98 | 79 | 19 | 80.61% | 98 | 88 | 10 | 89.80% |

The above results show that the traditional Chinese medicine compound composition in embodiment 3 of the disclosure had better therapeutic effect on degenerative osteoarthritis, and the cure rate reached 89.80% after taking it for 90 days.

(6) Adverse Reaction Observation

During the trial period, there were no adverse reactions or allergic reactions.

2. Effect of Treating Osteoporosis (1) Basic Information

It has been diagnosed that the symptoms of "soreness and weakness of waist and back after walking or activity, pain of waist and back in daily life, dizziness" were caused by osteoporosis or osteopenia. Other requirements are the same as above.

(2) Diagnostic Criteria

According to the back soreness after walking or activities, the symptoms were divided into grade I-IV, and the accumulate score were calculated.

Grade I (0): no sensation.

Grade II (1 point): slightly sour back after walking.

Grade III (2 points): feeling between grade II and grade IV.

Grade IV (3 points): weakness and soreness of waist and back, continuous occurrence, do not want to stand or walk.

(3) Treatment Methods and Course of Treatment 186 patients were randomly divided into group A and group B, with 93 patients in each group. Group A took the capsules of traditional Chinese medicine compound composition in embodiment 3, and group B took the capsules of traditional Chinese medicine compound composition in comparative embodiment 1, twice a day for each person, 2 capsules each time, with the dosage of 2.4 g/day for 90 consecutive days.

(4) Evaluation Criteria of Curative Effect

The same as above.

(5) Curative Effect a) Safety Observation

The results of white blood cells, red blood cells, hemoglobin and platelets showed no significant changes ($P>0.05$) before taking, 30 days and 90 days after taking; the results of heart rate showed no significant changes ($P>0.05$); chest X-ray, electrocardiogram, abdominal B-ultrasound and urine routine examination showed no significant abnormalities.

TABLE 7

Changes of symptom accumulate score before and after taking

| Time | Comparative embodiment 1 | Embodiment 3 |
|---|---|---|
| 0 day | 4.02 ± 2.71 | 4.02 ± 2.14 |
| 30 days | 3.45 ± 2.13* | 3.15 ± 1.88** |

TABLE 7-continued

Changes of symptom accumulate score before and after taking

| Time | Comparative embodiment 1 | Embodiment 3 |
|---|---|---|
| 60 days | 2.87 ± 1.76** | 2.46 ± 1.54**## |
| 90 days | 2.38 ± 2.01**## | 2.20 ± 1.54**## |

Note:
compared with 0 day
*P < 0.05,
**P < 0.01; compared with 30 days
P < 0.05,
P < 0.01; compared with 60 day
*P < 0.05.

TABLE 8

Overall efficacy evaluation

| Time/day | Comparative embodiment 1 | | | | Embodiment 3 | | | |
|---|---|---|---|---|---|---|---|---|
| | Number | Effective | invalid | Effective rate | Number | Effective | invalid | Effective rate |
| 7 | 93 | 12 | 81 | 12.90% | 93 | 16 | 77 | 17.20% |
| 14 | 93 | 20 | 73 | 21.51% | 93 | 28 | 65 | 30.11% |
| 21 | 93 | 28 | 65 | 30.11% | 93 | 38 | 55 | 40.86% |
| 30 | 93 | 34 | 59 | 36.56% | 93 | 43 | 50 | 46.24% |
| 45 | 93 | 42 | 51 | 45.16% | 93 | 51 | 42 | 54.84% |
| 60 | 93 | 57 | 36 | 61.29% | 93 | 64 | 29 | 68.82% |
| 90 | 93 | 64 | 29 | 68.82% | 93 | 69 | 24 | 74.19% |

The above results show that the traditional Chinese medicine compound composition disclosed by the disclosure had certain improving effect on the symptoms caused by bone mineral density reduction or osteoporosis, and the improvement effect increased with the extension of time. The effective rate was 74.19% after 90 days.

(6) Adverse Reaction Observation

During the trial period, there were no adverse reactions or allergic reactions. 3. Improvement of symptoms associated with cardiovascular and cerebrovascular diseases (1) Basic Information The patients were diagnosed with cardiovascular and cerebrovascular diseases, with chest pain, chest tightness, palpitations, unstable sleep or short time and other symptoms. Other requirements were the same as above.

(2) Diagnostic Criteria

According to the back soreness after walking or activities, the symptoms were divided into grade I-IV, and the accumulate score were calculated.

Grade I (0): no sensation.

Grade II (1 point): There are more typical attacks of angina pectoris, each lasting a few minutes, at least 2 to 3 times a week; or 1 to 3 times a day, but the pain is not serious, and sometimes requires mouth nitroglycerin; slight chest tightness; heart palpitations sometimes occur. But be competent for general daily activities, heart palpitations occur during slightly heavy physical activity; often wake up or sleep instability during sleep, wake up early in the morning, but does not affect life.

Grade III (2 points): Several typical attacks of angina pectoris a day, each lasting about 10 minutes, angina pectoris is serious, usually requires mouth nitroglycerin; chest tightness is obvious, sometimes sigh-like breathing; occasionally, normal daily activities may cause palpitations; sleep less than 4 hours. But be still able to stick to daily work.

Grade IV (3 points): Typical angina pectoris attacks occur many times a day, affecting daily life (such as defecation, clothing, etc.), each attack lasts for a long time, and requires nitroglycerin in mouth for many times; chest tightness such as asphyxia, sighing more than once; frequent occurrence, slight activity or palpitation without obvious reason; sleepless all night, it is difficult to adhere to normal life and work.

(3) Treatment Methods and Course of Treatment 174 patients were randomly divided into group A and group B, with 87 patients in each group. Group A took the capsules of traditional Chinese medicine compound composition in embodiment 3, and group B took the capsules of traditional Chinese medicine compound composition in comparative embodiment 1, twice a day for each person, 2 capsules each time, with the dosage of 2.4 g/day for 90 consecutive days.

(4) Evaluation Criteria of Curative Effect

The same as above.

(5) Curative Effect a) Safety Observation

The results of white blood cells, red blood cells, hemoglobin and platelets showed no significant changes (P>0.05) before taking, 30 days and 90 days after taking; the results of heart rate showed no significant changes (P>0.05); chest X-ray, electrocardiogram, abdominal B-ultrasound and urine routine examination showed no significant abnormalities.

TABLE 9

Changes of symptom accumulate score before and after taking

| Time | Comparative embodiment 1 | Embodiment 3 |
|---|---|---|
| 0 day | 2.90 ± 1.98 | 2.93 ± 2.17 |
| 30 days | 2.51 ± 2.01* | 2.34 ± 1.86* |
| 60 days | 2.13 ± 1.45* | 1.82 ± 1.58**# |
| 90 days | 1.79 ± 1.76** | 1.56 ± 1.48**## |

Note:
compared with 0 day
*P < 0.05,
**P < 0.01; compared with 30 days
P < 0.05,
P < 0.01; compared with 60 day
*P < 0.05.

TABLE 10

Improving effect on symptoms of various cardiovascular and cerebrovascular diseases

| | | Effective rate | |
|---|---|---|---|
| time | Project | Comparative embodiment 1 | Embodiment 3 |
| 30 days | Chest tightness | 37.12% | 40.00% |
| | Chest pain | 28.55% | 31.67% |
| | Palpitation | 20.36% | 23.08% |
| | Light sleep or short sleep | 22.46% | 25.37% |
| 60 days | Chest tightness | 51.23% | 60.00% |
| | Chest pain | 48.65% | 55.00% |
| | Palpitation | 50.12% | 52.31% |
| | Light sleep or short sleep | 47.65% | 50.75% |
| 90 days | Chest tightness | 58.77% | 63.33% |
| | Chest pain | 59.36% | 63.64% |
| | Palpitation | 56.23% | 61.54% |
| | Light sleep or short sleep | 57.66% | 62.69% |

TABLE 11

Overall efficacy evaluation

| | Comparative embodiment 1 | | | | Embodiment 3 | | | |
|---|---|---|---|---|---|---|---|---|
| Time/day | Number | Effective | invalid | Effective rate | Number | Effective | invalid | Effective rate |
| 7 | 87 | 9 | 78 | 10.34% | 87 | 15 | 72 | 17.24% |
| 14 | 87 | 16 | 71 | 18.39% | 87 | 24 | 63 | 27.59% |
| 21 | 87 | 24 | 63 | 27.59% | 87 | 33 | 54 | 37.93% |
| 30 | 87 | 28 | 59 | 32.18% | 87 | 37 | 50 | 42.53% |
| 45 | 87 | 40 | 47 | 45.98% | 87 | 52 | 35 | 59.77% |
| 60 | 87 | 49 | 38 | 56.32% | 87 | 59 | 28 | 67.82% |
| 90 | 87 | 56 | 31 | 64.37% | 87 | 60 | 27 | 68.97% |

The above results show that the traditional Chinese medicine compound composition disclosed by the disclosure assisted in improving the symptoms of cardiovascular disease, and the improving effect increased with the extension of time. The effective rate was 68.97% after 90 days.

(6) Adverse Reaction Observation

During the trial period, there were no adverse reactions or allergic reactions.

4. Effect of Treatment of Hypertension (Systolic Blood Pressure, Diastolic Blood Pressure, Etc.)

(1) Basic Information

A total of 160 patients with hypertension, aged 50-75 years, were collected. Other requirements were the same as above.

(2) Treatment Methods and Course of Treatment 160 patients were randomly divided into group A and group B, with 80 patients in each group. Group A took the capsules of traditional Chinese medicine compound composition in embodiment 3, and group B took the capsules of traditional Chinese medicine compound composition in comparative embodiment 1, twice a day for each person, 2 capsules each time, with the dosage of 2.4 g/day for 90 consecutive days.

(3) Evaluation Criteria of Curative Effect

1) Cure: after a course of treatment, blood pressure, blood lipid and blood glucose returned to normal;

2) Effective: blood pressure has decreased or tends to be normal;

3) Invalid: no improvement of symptoms.

(4) Curative effect

TABLE 12

Changes of vascular regulatory factors

| | | Effective rate | |
|---|---|---|---|
| Time | Project | Comparative embodiment 1 | Embodiment 3 |
| 0 day | Nitric oxide (NO) | 2.12 ± 0.34 | 2.12 ± 0.24 |
| | Endothelin (ET) | 28.15 ± 15.55 | 28.14 ± 15.74 |
| | Angiotensin II (Ang~II) | 76.98 ± 15.69 | 76.99 ± 19.24 |
| | Vascular endothelial growth factor (VEGF) | 83.30 ± 62.36 | 83.30 ± 72.63 |
| 30 days | Nitric oxide (NO) | 14.32 ± 5.69* | 16.44 ± 13.41* |
| | Endothelin (ET) | 18.55 ± 8.96** | 16.61 ± 8.45** |

TABLE 12-continued

Changes of vascular regulatory factors

| | | Effective rate | |
|---|---|---|---|
| Time | Project | Comparative embodiment 1 | Embodiment 3 |
| | Angiotensin II (Ang~II) | 79.12 ± 18.66** | 80.23 ± 17.34 |
| | Vascular endothelial growth factor (VEGF) | 91.86 ± 74.56** | 100.36 ± 91.24 |
| 90 days | Nitric oxide (NO) | 17.23 ± 5.96* | 18.86 ± 6.64* |
| | Endothelin (ET) | 11.17 ± 7.98* | 9.12 ± 8.96* |
| | Angiotensin II (Ang~II) | 78.32 ± 18.90# | 76.42 ± 13.77# |
| | Vascular endothelial growth factor (VEGF) | 82.12 ± 41.22# | 80.34 ± 34.36# |

Note:
compared with 0 day,
*P < 0.05,
**P < 0.01; compared with day 30,
P < 0.05. The number of cases of nitric oxide (no) and endothelin (ET) was 17, the number of cases of angiotensin II (Ang - II) and vascular endothelial growth factor (VEGF) was 35.

TABLE 13

Changes of blood pressure before and after taking

| Time | Project | Detection value | | Decline rate | | Effective rate | |
|---|---|---|---|---|---|---|---|
| | | Comparative embodiment 1 | Embodiment 3 | Comparative embodiment 1 | Embodiment 3 | Comparative embodiment 1 | Embodiment 3 |
| 0 day | systolic | 152.69 ± 18.04 | 152.69 ± 18.04 | ~ | ~ | ~ | ~ |
| | diastolic | 81.45 ± 9.92 | 81.45 ± 9.92 | ~ | ~ | ~ | ~ |
| 30 days | systolic | 147.85 ± 19.32 | 146.94 ± 18.19 | 3.98% ± 9.68% | 4.46% ± 10.23% | 65.32% | 70.51% |
| | diastolic | 80.97 ± 10.11 | 80.41 ± 9.94 | 3.15% ± 9.11% | 3.72% ± 8.76% | 51.23% | 57.69% |
| 90 days | systolic | 143.77 ± 18.54 | 140.94 ± 17.69 | 7.35% ± 10.65% | 8.64% ± 9.51% | 69.33% | 76.25% |
| | diastolic | 77.56 ± 11.96 | 76.31 ± 10.14 | 6.11% ± 9.74% | 7.21% ± 9.19% | 64.85% | 73.75% |

The above results show that the Chinese medicine compound composition reduced blood pressure to a certain extent, increased the vasodilator factor "nitric oxide (NO)" and reduced the vasoconstrictor factor "endothelin (ET)". At the same time, after taking 90 days, the effective rates of diastolic blood pressure and systolic blood pressure were 73.75% and 76.24% respectively.

(5) Adverse Reaction Observation

During the trial period, there were no adverse reactions or allergic reactions.

5. Improvement of the Symptoms of Urinary System Diseases (1) Basic Information

The patients were diagnosed with cardiovascular and cerebrovascular diseases, with chest pain, chest tightness, palpitations, sleep is not stable or short time and other symptoms. Other requirements were the same as above.

(2) Diagnostic Criteria

Benign prostatic hyperplasia: there were 4 items (frequency of urination, urgency of urination, pain of urination, and incompleteness of urination). According to the severity of symptoms, the symptoms were divided into grade I-IV, and the accumulate score were calculated.

Grade I (0): asymptomatic, normal.

Grade II (1 point): increased frequency of urination, 2 times of nocturia; urgency of urination, but tolerable; dull pain in urethra during urination, which does not affect urination; occasionally slight incontinence.

Grade III (2 points): increased frequency of urination, 3-4 times of nocturia; urgency of urination, can only endure for a moment; severe urethral pain and poor urination; obvious intermittent, and incomplete urination.

Grade IV (3 points): increased frequency of urination, more than 5 times of nocturia; urgent urination, can't wait; unbearable urethral pain during urination; continuous frequent urination.

(3) Treatment Methods and Course of Treatment 162 patients were randomly divided into group A and group B, with 81 patients in each group. Group A took the capsules of traditional Chinese medicine compound composition in embodiment 3, and group B took the capsules of traditional Chinese medicine compound composition in comparative embodiment 1, twice a day for each person, 2 capsules each time, with the dosage of 2.4 g/day for 90 consecutive days.

(4) Evaluation Criteria of Curative Effect

The same as above.

(5) Curative Effect a) Safety Observation

The results of white blood cells, red blood cells, hemoglobin and platelets showed no significant changes ($P>0.05$) before taking, 30 days and 90 days after taking; the results of heart rate showed no significant changes ($P>0.05$); chest X-ray, electrocardiogram, abdominal B-ultrasound and urine routine examination showed no significant abnormalities.

TABLE 14

Changes of symptom accumulate score before and after taking

| Time | Comparative embodiment 1 | Embodiment 3 |
|---|---|---|
| 0 day | 2.92 ± 2.31 | 2.91 ± 2.30 |
| 30 days | 2.43 ± 1.45* | 2.25 ± 1.79* |
| 60 days | 2.13 ± 1.27* | 1.84 ± 1.64** |
| 90 days | 1.83 ± 1.44** | 1.61 ± 1.56***## |

Note:
compared with 0 day
*$P < 0.05$,
**$P < 0.01$; compared with 30 days
$P < 0.05$,
$P < 0.01$; compared with 60 day
*$P < 0.05$.

TABLE 15

Overall efficacy evaluation

| Time/day | Comparative embodiment 1 | | | | Embodiment 3 | | | |
|---|---|---|---|---|---|---|---|---|
| | Number | Effective | invalid | Effective rate | Number | Effective | invalid | Effective rate |
| 7 | 81 | 11 | 70 | 13.58% | 81 | 15 | 66 | 18.52% |
| 14 | 81 | 18 | 63 | 22.22% | 81 | 22 | 59 | 27.16% |
| 21 | 81 | 25 | 56 | 30.86% | 81 | 28 | 53 | 34.57% |
| 30 | 81 | 27 | 54 | 33.33% | 81 | 31 | 50 | 38.27% |
| 45 | 81 | 34 | 47 | 41.98% | 81 | 39 | 42 | 48.15% |
| 60 | 81 | 42 | 39 | 51.85% | 81 | 47 | 34 | 58.02% |
| 90 | 81 | 53 | 28 | 65.43% | 81 | 62 | 19 | 76.54% |

(6) Adverse Reaction Observation

During the trial period, there were no adverse reactions or allergic reactions. In addition, in other embodiments, the traditional Chinese medicine compound composition disclosed by the disclosure is prepared into decoction, granule, pill, capsule and oral liquid through conventional methods, which has consistent therapeutic effect.

It can be seen from the above analysis that the disclosure has significant curative effect on the treatment of degenerative osteoarthritis, osteoporosis, cardiovascular and cerebrovascular diseases, reproductive system diseases and hypertension, and is safe to take; and the traditional Chinese medicine compound composition disclosed in the disclosure can be made into a variety of dosage forms to meet the needs of different patients, and is suitable for market promotion and application.

Described above are merely illustrative of the disclosure to enable those skilled in the art to implement or use the disclosure, and are not intended to limit the disclosure. It should be understood that any modification, replacement and change made by those skilled in the art without departing from the spirit of the disclosure should fall within the scope of the disclosure.

What is claimed is:

1. A multi-efficacy traditional Chinese medicine compound composition, composed of the following raw materials in parts by weight:
   0.5 to 2.0 parts of glucosamine;
   0.5 to 1.5 parts of collagen;
   0.1 to 1.0 parts of chondroitin sulfate; and
   0.3 to 1.5 parts of traditional Chinese medicine extracts;
   wherein the traditional Chinese medicine extracts is a mixture composed of *Epimedii Folium* extract, *Salvia Miltiorrhizae* extract, and *Dioscoreae Nipponicae Rhizoma* extract; wherein the traditional Chinese medicine extracts are prepared by extracting traditional Chinese medicine; the traditional Chinese medicine comprises the following components in parts by weight:
   25 to 40% of *Epimedii Folium* extract;
   3 to 7% of *Salvia Miltiorrhizae* extract; and
   50 to 75% of *Dioscoreae Nipponicae Rhizoma* extract.

2. The multi-efficacy traditional Chinese medicine compound composition of claim 1, composed of the following raw materials in parts by weight:
   0.7 to 1.0 parts of glucosamine;
   0.5 to 0.8 parts of collagen;
   0.2 to 0.5 parts of chondroitin sulfate; and
   0.5 to 0.7 parts of traditional Chinese medicine extracts.

3. The multi-efficacy traditional Chinese medicine compound composition of claim 1, composed of the following raw materials in parts by weight:
   0.8 parts of glucosamine;
   0.6 parts of collagen;
   0.3 parts of chondroitin sulfate; and
   0.55 parts of traditional Chinese medicine extracts.

4. The multi-efficacy traditional Chinese medicine compound composition of claim 1, wherein the traditional Chinese medicine extracts are composed of following extracts according to the mass percentage:
   25 to 34% of *Epimedii Folium* extract;
   4 to 4.8% of *Salvia Miltiorrhizae* extract; and
   55 to 70% of *Dioscoreae Nipponicae Rhizoma* extract.

5. The multi-efficacy traditional Chinese medicine compound composition of claim 1, wherein an extraction process of the *Dioscoreae Nipponicae Rhizoma* extract comprises the following steps:
   1) subjecting *Dioscoreae Nipponicae Rhizoma* material to extraction with a 50-70% ethanol solution in a volume ratio of 1:7 to 1:15, heating reflux 2 to 3 times for 1 to 2 h each time and filtration to obtain filtrates;
   2) combining the filtrates, purifying, concentrating, and adding with 10% β-cyclodextrinto; continuously subjecting the combined filtrate to spray drying at 200° C.; and sieving the dried product with a sieve of 80 mesh to produce the *Dioscoreae Nipponicae Rhizoma* extract.

6. The multi-efficacy traditional Chinese medicine compound composition of claim 5, wherein an extraction process of the *Dioscoreae Nipponicae Rhizoma* extract comprises the following steps:
   1) subjecting *Dioscoreae Nipponicae Rhizoma* material to extraction with a 70% ethanol solution in a volume ratio of 1:15, heating reflux twice for 2 h each time and filtration to obtain filtrates;
   2) combining the filtrates, purifying, concentrating, and adding with 10% β-cyclodextrinto; continuously subjecting the combined filtrate to spray drying at 200° C.; and sieving the dried product with a sieve of 80 mesh to produce the *Dioscoreae Nipponicae Rhizoma* extract.

* * * * *